(12) United States Patent
Eising (10) Patent No.: US 9,891,155 B2
(45) Date of Patent: Feb. 13, 2018

(54) COULTER MOUNTED SOIL CONSTITUENT SENSOR

(71) Applicants: Erik Eising, Winnipeg (CA); David A. Prystupa, Pinawa (CA)

(72) Inventor: Erik Eising, Winnipeg (CA)

(73) Assignee: 7108789 Manitoba Inc., Winnipeg, MB (CA)

( * ) Notice: Subject to any disclaimer, the term of this patent is extended or adjusted under 35 U.S.C. 154(b) by 0 days.

(21) Appl. No.: 14/545,583

(22) Filed: May 26, 2015

(65) Prior Publication Data
US 2016/0349167 A1    Dec. 1, 2016

Related U.S. Application Data

(60) Provisional application No. 61/997,139, filed on May 23, 2014.

(51) Int. Cl.
*G01N 15/06* (2006.01)
*G01N 21/65* (2006.01)
(Continued)

(52) U.S. Cl.
CPC .......... *G01N 15/06* (2013.01); *A01B 79/005* (2013.01); *A01C 21/007* (2013.01); *G01J 3/44* (2013.01);
(Continued)

(58) Field of Classification Search
CPC .... G01N 15/06; G01N 15/1434; G01N 21/65; G01N 2015/0693; G01N 2021/656;
(Continued)

(56) References Cited

U.S. PATENT DOCUMENTS

| | | | |
|---|---|---|---|
| 7,547,904 B2 * | 6/2009 | Schmidt | B01L 3/502715 250/573 |
| 8,451,449 B2 | 5/2013 | Holland | |

(Continued)

OTHER PUBLICATIONS

"Book of Farm" to Henry Stephens (1854), pp. 271-273 and Bacon, Charles Allen (1920), "The Oliver plow book: a treatise on plows and plowing" p. 163; recovered from reference [1] and [2] respectively of https://en.wikipedia.org/wiki/Coulter_ (agriculture)#cite_note-BookOfTheFarm-1.*

(Continued)

*Primary Examiner* — Tarifur Chowdhury
*Assistant Examiner* — Mohamed K Amara
(74) *Attorney, Agent, or Firm* — Adrian D. Battison; Ade & Company Inc; Michael R. Williams (57) ABSTRACT

A system for measuring soil constituents having coulter comprising an electromagnetic radiation detector, a source of electromagnetic radiation, and a window transparent to electromagnetic radiation, the source emits radiation through said window to the soil, and the detector receives radiation through said window, reflected from the soil. Typically the source is broad band so the detector provides continuous spectra over the range. The source may be quasimonochromatic to provide Raman scattering, which will also provide continuous spectra over the range. These spectra can be subjected to multivariate analysis and compared to spectra of known constituents to identify the presence and concentration of these constituents.

19 Claims, 5 Drawing Sheets

(51) Int. Cl.
  *A01B 79/00* (2006.01)
  *G01J 3/44* (2006.01)
  *A01C 21/00* (2006.01)
  *G01N 21/3563* (2014.01)
  *G01N 21/552* (2014.01)
  *G01N 15/14* (2006.01)
  *G01N 33/24* (2006.01)

(52) U.S. Cl.
  CPC ..... *G01N 15/1459* (2013.01); *G01N 21/3563* (2013.01); *G01N 21/552* (2013.01); *G01N 21/65* (2013.01); *G01N 15/1434* (2013.01); *G01N 2015/0693* (2013.01); *G01N 2033/245* (2013.01)

(58) Field of Classification Search
  CPC .. G01N 15/1459; G01N 21/658; G01N 21/64; G01N 2021/653; G01N 21/53; G01N 21/359; G01N 21/6458; G01N 2021/655
  See application file for complete search history.

(56) References Cited

U.S. PATENT DOCUMENTS

| | | | |
|---|---|---|---|
| 2002/0039186 A1* | 4/2002 | Rosenberg | G01J 3/02 356/432 |
| 2002/0131046 A1* | 9/2002 | Christy | G01N 21/15 356/445 |
| 2012/0324986 A1* | 12/2012 | Chekalyuk | G01J 3/02 73/61.52 |

OTHER PUBLICATIONS http://summersmfg.com/media/1182/coulterchisel-blades.png?width=435&height=290 or http://thurstonmfg.co/wp-content/uploads/2014/01/Picture1.png.*
http://www.gatesmfg.net/products/coulter-disc/ (Photo Gallery section).*

* cited by examiner

COULTER MOUNTED SOIL CONSTITUENT SENSOR

FIELD OF THE INVENTION

The present invention is directed to an emitter and sensor system to assess soil quality and condition including soil constituents mounted in a coulter disc. The emitter is electromagnetic typically which may be in the ultraviolet or visible range, but more typically in the near or middle infrared range. The emitted light is reflected by the soil and the absorbances at various wavelengths measured, these absorbances enable identification of substances present in the soil, typically but not restricted to soil constituents.

The device of the invention provides a means for real-time soil analysis. The invention is directed toward three types of application: agricultural, environmental and mineral.

For agriculture, the device can be mounted on a self propelled vehicle or towed agricultural equipment such as seeders, planters, manure applicators etc. The data collected by the device can be processed to determine application rates for precision agricultural systems such as variable rate seeding and variable rate fertilizer application. The invention is an improvement on existing technology that uses sensors mounted on a shank. The device causes less soil disturbance, requires less power to tow, and can be operated under less favourable weather and soil conditions. The device collects data for a continuous profile, possibly at millimeter resolution rather than at a few points 50-100 mm apart. Further, because the device collects data at finite intervals both above and below the surface the soil composition depth profile is relative to the actual surface. The device can be used in till, no till and pasture contexts The device can be used to determine the concentration of chemical contaminants in soil as a function of depth for environmental remediation. The cause of contamination could be, for example, a crude oil spill onto a body of water that subsequently washes onto sandy beaches. In another example, the contamination could be PCB's from an electrical transformer site. In another example, the contamination could be pesticides or herbicides proximate to a manufacturing or storage facility. In another example, the contamination could be colloidal minerals discharged from a coal burning power plant. In another example, the contamination could be metals such as lead or arsenic proximate to industrial or mining sites. In each case, the device could be used to measure the extent and depth of contamination, which would become the basis for plans to treat the affected volume of sand or soil. The device could be used a second time to measure the effectiveness of the remediation procedure. The device can also be used to measure the carbon content in soil and the information can be used as the basic for determining carbon credits The device can be used to prospect for minerals and hydrocarbons. Minerals from a deposit are washed by water into surrounding soils. The device can be used to measure the concentration of a target mineral in soil over a suspected area. The concentration gradient can be used to infer the location of the original deposit for conventional extraction by mining. Information about the concentration of the target mineral in soil can also be used to plant crops that preferentially extract that mineral from soil.

BACKGROUND OF THE INVENTION

Numerous devices and methods are known for measurement of soil constituents, but in general this cannot be done in real time when seeding or fertilizing soil. It is known to use an instrumented disc coulter (3 feet, 76 cms, in diameter) using a rotary potentiometer and an ultrasound proximity sensor, as soil mechanical resistance and depth measurement. Basically the proposed invention measures constituents in situ, in vivo, in real time. The measuring system may be connected wirelessly or hard wired via the axle of the coulter to data processing system connected to a computerised control system in the tractor cab. The constituent data can be processed to modify seeding of the soil, or fertilizer deposition in the soil as seeding and fertilizer deposition are performed.

PRIOR ART

The measurement of soil constituents by electromagnetic radiation is old and known and an extensive scientific and patent literature exists in this field. The closest prior art appears to applicant to be U.S. Pat. No. 8,451,449 to Holland, 28 May 2013. Holland teaches to measure reflectance of sub surface soil by dragging a device containing a light source and sensor below the soil surface, both light source and sensor are with the device and light is emitted and received through a light transparent window which is scratch resistant to soil. The soil has to be disturbed prior to measurement either by a tillage device pulled ahead of the sensor for subsurface measurement or by passing the sensor over previously tilled soil. The sensor measures light reflected back from the soil then using a mathematical equation for different classes of soil, each equation has parameters determined by the local landscape, described as an auto calibration algorithm based on average organic content of the landscape. The light source is described as one or many banks of polychromatic or monochromatic LEDs or laser diodes at considerable length. The photodector or photodetector array are photodiodes, which may further involve filters. The photodetector output is amplified with a transconductance amplifier having a feedback servo to cancel the effects of ambient light, and allows only modulated reflectance optical signals to pass to further instrumentation. Phase sensitive detector circuits and analog-digital converters are used, which amplify small signals from the background noise. The resultant reflectant signals are then processed signals are then normalized using at least two wavelengths to generate components which can be used to identify soil constituents In general a plurality of wavelengths are used.

SUMMARY OF THE INVENTION

The invention is an electromagnetic radiation emitter and detector mounted in a coulter, a windowed aperture allows the radiation to interact with the soil. The resultant reflected radiation is measured by the detector to produce a continuous spectrum which is much more informative, the spectrum is then compared to a data base or library of spectra of known constituents and thus determine soil constituents. Except for Raman spectrometry broad band emitters are used such as deuterium lamps, quartz-halogen bulbs or heated wires, such as Ni-Chrome. In Raman spectroscopy a quasi-monochromatic source is used, however as those skilled the art will appreciate a continuous spectrum is thereby generated and measured. The coulter cuts smoothly into the soil with minimal disturbance, even into heavy and sodden soil. The depth is variable sampling several subsoil levels. The continuous spectrum over the range of wavelength provides more information and allows statistical analysis of spectra both in real time and later as stored data.

OBJECTS OF THE INVENTION

The principal object of the invention is to assess soil quality. A further principal object of the invention is to provide a system for measuring soil constituents including a coulter comprising a sensor comprising an electromagnetic radiation detector. A subsidiary object is to provide a system including a coulter comprising a sensor comprising a source of electromagnetic radiation. A further subsidiary object of the invention is to provide a system wherein said sensor comprises a window transparent to electromagnetic radiation, the source emits radiation into the window, and the detector receives radiation from the window. A further principal object of the invention is to provide a plurality of sensors, arranged so that at least one sensor is below ground during use of the coulter at any one time. A subsidiary object of the invention is to provide sensors equispaced radially around the axis of said coulter. A further subsidiary object of the invention is to provide a system having an electromagnetic radiation detector which detects infrared radiation, selected from the group consisting of near infrared and mid infrared radiation. Another subsidiary object of the invention is to provide an electromagnetic radiation detector which detects Raman scattered radiation. An auxiliary object of the invention is to provide a system having an electromagnetic radiation detector comprising a wavelength selector and an optical detector. A further auxiliary object of the invention is to provide a system wherein the wavelength selector is selected from the group consisting of a prism, a diffraction grating, and a multiple diffraction grating and the optical detector is selected from a linear pixel array and a sensitive photon counter coupled with an amplifier. A further auxiliary object of the invention is to provide a system wherein the electromagnetic radiation detector is a Fourier transform spectrometer, the spectrometer being simultaneously both a wave selector and an optical detector. A further auxiliary object of the invention is to provide a system having a source of electromagnetic radiation to emit near infrared and the electromagnetic radiation detector is selected from the group consisting of a prism coupled with multi-element photon detector, a movable prism coupled with a single detector a fixed diffraction grating coupled with a multi-element detector and a movable diffraction grating coupled with a single detector. A further auxiliary object of the invention is to provide a system having a source of electromagnetic radiation to emit mid infrared and the electromagnetic radiation detector is selected from the group consisting of a fixed diffraction grating coupled with a multi-element detector and a movable diffraction grating coupled with a single detector and a Fourier transform spectrometer. A further auxiliary object of the invention is to provide a system having a source of electromagnetic radiation which is selected from the group consisting of a gas laser, and a semiconductor laser in conjunction with at least one band pass filter and a LED in conjunction at least two band pass filters to emit a quasimonochromatic wavelength selected from the group consisting of ultraviolet, visible and near infrared the electromagnetic radiation detector is selected from the group consisting of a prism coupled with a multi-element photon detector, a movable prism coupled with a single detector, a diffraction grating coupled with a multi-element photon detector, and a movable diffraction grating coupled with a single photon detector and a Fourier transform spectrometer. Another auxiliary object of the invention is to provide a system wherein the electromagnetic radiation detector supplies spectral data to a data processor which is adapted to subject the data to multivariate analysis and compare that data to data in a calibration set to determine the concentration of soil constituents, preferably the detector is connected to the processor by electrical wire, fibre optical cable, or wireless.

A further subsidiary object of the invention is to provide a window selected from the group consisting of $CaF_2$, $BaF_2$, quartz, silica, sapphire, ruby, diamond, KBr, NaCl, KCl, glass, AgCl, AgBr, KRS-5 (thallium bromiodide), ZnSe, GaAs, ZnS, CsBr, CsI, PTFE, PE, silicon, ZnSe, CdTe, PE and Ge (IR transmitting polymers such as PE may be used). Preferably this window is on the exterior of the coulter. Another subsidiary object of the invention is to provide a system wherein the window is selected from the group consisting $CaF_2$, $BaF_2$, silica, quartz, sapphire, and ZnSe, and there is a source of electromagnetic radiation selected from the group consisting of a gas laser, and a semiconductor laser in conjunction with at least one band pass filter and a LED in conjunction at least two band pass filters emitting a quasimonochromatic wavelength selected from the group consisting of ultraviolet, visible and near infrared, and there is a electromagnetic radiation detector is selected from the group consisting of a prism coupled with multi-element photon detector, a movable prism coupled with a single detector, a diffraction grating coupled with a multi-element photon detector, and a movable diffraction grating coupled with a single photon detector and a Fourier transform spectrometer. Another subsidiary object of the invention is to provide a system with a window selected from the group consisting of diamond, KBr, NaCl, KCl, $CaF_2$, $BaF_2$, glass, silica, quartz, sapphire, AgCl, AgBr, KRS-5 (thallium bromiodide), ZnSe, GaAs, and ZnS and there is a source of electromagnetic radiation to emit near infrared and the electromagnetic radiation detector is selected from the group consisting of a prism coupled with multi-element photon detector, a movable prism coupled with as single detector, a fixed diffraction grating coupled with a multi-element detector and a movable diffraction grating coupled with a single detector. Another subsidiary object of the invention is to provide a system with a window is selected from the group consisting of KBr, CsBr, CsI, NaCl, KCl, $CaF_2$, $BaF_2$, PTFE, PE, silicon, AgCl, AgBr, KRS-5 (thallium bromiodide), ZnSe, Ge and CdTe and there is a source of electromagnetic radiation to emit mid infrared and an electromagnetic radiation detector is selected from the group consisting of a fixed diffraction grating coupled with a multi-element detector and a movable diffraction grating coupled with a single detector and a Fourier transform spectrometer. Preferably the window is in a recess in the coulter, and more preferably a fluid which is optically transparent to the electromagnetic radiation, is supplied to the recess, through an orifice at a pressure higher than the surrounding soil pressure, whereby it oozes into and fills the recess between window and soil at a flow rate sufficient to keep the window clear. Alternatively a nozzle supplies water periodically as a jet directed at the window, activated at or near the top of its arc of travel, to clean the window when soiled in a cleaning cycle. The coulter may comprises a reservoir for water for the nozzle and water is supplied from the reservoir to the nozzle by a member selected from the group consisting of an electrical pump, a mechanical pump and a Bernoulli effect device. Another subsidiary object of the invention is to provide a system with a window selected from the group consisting of diamond, KBr, NaCl, KCl, $CaF_2$, $BaF_2$, glass, PE, silica, quartz, sapphire, AgCl, AgBr, KRS-5 (thallium bromiodide), ZnSe, GaAs, and ZnS and there is a source of electromagnetic radiation to emit near infrared through the window and the electromagnetic radiation detector is selected from the group consisting of a prism coupled with multi-element photon detector, a movable prism coupled with a single detector, a fixed diffraction grating coupled with a multi-element detector and a movable diffraction grating coupled with a single detector. Another subsidiary object of the invention is to provide a system with a window selected from the group consisting of KBr, CsBr, CsI, NaCl, KCl, $CaF_2$, $BaF_2$, PTFE, PE, silicon, AgCl, AgBr, KRS-5 (thallium bromiodide), ZnSe, Be and CdTe and germanium, there is a source of electromagnetic radiation to emit mid infrared through the window and an electromagnetic radiation detector is selected from the group consisting of a fixed diffraction grating coupled with a multi-element detector and a movable diffraction grating coupled with a single detector and a Fourier transform spectrometer, detects radiation reflected through the window. Preferably the window is in the interior of the coulter and there is a recess in the coulter and a nozzle for water has output from the recess to provide a jet of water to induce a slurry to form in the recess and an aspirator in the recess to suck the slurry through a flow cell in the coulter, the window forming a wall of the flow cell, and an channel from the flow cell to an external orifice in the coulter. More preferably the coulter comprises a reservoir for water for the nozzle and the water is supplied from the reservoir to the nozzle by a member selected from the group consisting of an electrical pump, a mechanical pump and a Bernoulli effect device. Another subsidiary object of the invention is to provide a system with a window selected from the group consisting of $CaF_2$, $BaF_2$, silica, quartz, sapphire, and ZnSe, there is a source of electromagnetic radiation which is selected from the group consisting of a gas laser, and a semiconductor laser in conjunction with at least one band pass filter and a LED in conjunction at least two band pass filters to emit a quasimonochromatic wavelength selected from the group consisting of ultraviolet, visible and near infrared emits radiation through the window, and a electromagnetic radiation detector selected from the group consisting of a prism coupled with multi-element photon detector, a movable prism coupled with a single detector, a diffraction grating coupled with a multi-element photon detector, and a movable diffraction grating coupled with a single photon detector and a Fourier transform spectrometer, detects radiation reflected through the window. Another subsidiary object of the invention is to provide a system with a window selected from the group consisting of diamond, KBr, NaCl, KCl, $CaF_2$, $BaF_2$, glass, PE, silica, sapphire, AgCl, AgBr, KRS-5 (thallium bromiodide), ZnSe, GaAs, and ZnS, there is a source of electromagnetic radiation to emit near infrared through the window and the electromagnetic radiation detector is selected from the group consisting of a prism coupled with multi-element photon detector, a movable prism coupled with a single detector, a fixed diffraction grating coupled with a multi-element detector and a movable diffraction grating coupled with a single detector, detects radiation reflected through the window. Another subsidiary object of the invention is to provide a system with a window selected from the group consisting of KBr, CsBr, CsI, NaCl, KCl, $CaF_2$, $BaF_2$, PTFE, PE, silicon, AgCl, AgBr, KRS-5 (thallium bromiodide), ZnSe, Ge and CdTe, and a source of electromagnetic radiation to emit mid infrared through the window and an electromagnetic radiation detector is selected from the group consisting of a fixed diffraction grating coupled with a multi-element detector and a movable diffraction grating coupled with a single detector and a Fourier transform spectrometer, detects radiation reflected through the window. Another subsidiary object of the invention is to provide a system with a window integral to an ATR (attenuated total internal reflection) flow cell and the window is selected from the group consisting of germanium, silicon, ZnSe, and KRS-5 (thallium bromiodide) and there is a source of electromagnetic radiation to emit mid infrared through the window and an electromagnetic radiation detector is selected from the group consisting of a fixed diffraction grating coupled with a multi-element detector and a movable diffraction grating coupled with a single detector and a Fourier transform spectrometer, detects radiation reflected through the window.

Another principal object of the invention is to provide a method of measuring soil constituents comprising the step of rotating a coulter having a window substantially transparent to electromagnetic radiation and the step of passing input electromagnetic radiation into the window, when the window is below soil surface level and allowing the radiation to interact with a sample of soil and the step of measuring the amplitude of resultant output electromagnetic the step of measuring the output amplitudes as a function of wavelength and the step of comparing the output amplitudes to input amplitudes as a function of wavelength as ratios to generate a characteristic spectrum and the step of comparing the output spectrum to known output spectra generated by standard samples of known constituents by multivariate analysis thereby identifying the presence and concentration of the constituents. An auxiliary object of the invention is to provide a method wherein the resultant output electromagnetic radiation is generated by a step selected from group consisting of diffuse reflectance from soil, transmission through a soil slurry in a flow cell, and attenuated total internal reflection at a window soil slurry interface of a flow cell and Raman scattering. An auxiliary object of the invention is to provide a method comprising the step of separately calculating an output amplitude for a narrow interval of wavelength to give an absorbance value for each the wavelength interval. An auxiliary object of the invention is to provide a method wherein input electromagnetic radiation is selected from the group consisting of UV, visible, near infrared and middle infrared. A further auxiliary object of the invention is to provide a method wherein the input electromagnetic radiation is near infrared. A further auxiliary object of the invention is to provide a method wherein the input electromagnetic radiation is middle infrared. A further auxiliary object of the invention is to provide a method wherein the input electromagnetic radiation is quasimonochromatic and selected from the group consisting of UV, visible and near infrared and the output electromagnetic radiation is Raman scattered. A further auxiliary object of the invention is to provide a method comprising the step of dispersing the output electromagnetic radiation through a wavelength selector to separate it into distinct wavelength intervals and the further step of measuring the amplitudes of the distinct wavelength intervals. A further auxiliary object of the invention is to provide a method comprising the step of collimating the input electromagnetic radiation. A further auxiliary object of the invention is to provide a method comprising the step of collimating the output electromagnetic radiation.

DESCRIPTION OF THE INVENTION

The invention has at least one light emitter and at least one light detector mounted in the coulter. These are linked by electronic or electromagnetic means to a data acquisition device. The data as supplied is typically analog in form although it may be converted to digital by an analog-digital converter. The data is then processed by a central processor. The output of the data processor is analyzed by comparison with a multivariate calibration model based on known calibration measurements derived from a library of existing measurements to give figures for soil constituents.

In general the invention comprises a coulter which has an electromagnetic radiation detector, a source of electromagnetic radiation, and a window transparent to electromagnetic radiation, the source emits radiation through the window to the soil, and the detector receives radiation through the window, reflected from the soil. A solid or hollow wave guide conveniently links window to detector.

Both emitter and detector typically operate via a window. Commercially viable and available off-the-shelf materials are preferred. In general the emitter is confined to UV, visible, NIR or MIR, and in the case of absorbance spectra the detector is similarly confined. Suitable window materials for UV are $CaF_2$, $BaF_2$, quartz, silica, sapphire and ruby. Suitable window materials for visible are diamond, KBr, NaCl, KCl, $CaF_2$, $BaF_2$, glass, silica, and sapphire. Suitable window materials for NIR are diamond, KBr, NaCl, KCl, $CaF_2$, $BaF_2$, glass, PE, silica, quartz, sapphire, AgCl, AgBr, KRS-5 (thallium bromiodide), ZnSe, GaAs, and ZnS. Suitable window materials for MIR are KBr, CsBr, CsI, NaCl, KCl, $CaF_2$, $BaF_2$, PTFE, PE, silicon, AgCl, AgBr, KRS-5 (thallium bromiodide), ZnSe, Ge and CdTe. Hygroscopic and soft material may be coated with CSi to waterproof and harden it. High refractive index materials such as germanium, silicon, zinc selenide, KRS-5 (thallium bromiodide) may be used for ATR (attenuated total internal reflection), $MgF_2$ may be used to coat input and output faces but not sample faces in ATR. ZnSe is preferably used as a window in NIR and MIR.

The window may be flush, especially if sapphire, with the surface of the typically metal coulter. If so the soil contacting the window may generate microscratches which distort the spectral signal. Otherwise window may be recessed typically about 3 mm (⅛ in), if the coulter rotation is faster than the viscoelastic response of the soil, then soil does not move into the recess and the window remains clear, except in muddy conditions, in which case it may be obscured by mud seeping into the recess.

Alternatively positive pressure may be provided in the recess to prevent soil moving into the recess, by a fluid which is optically transparent in the wavelength region of interest. The fluid is typically water or gel, conveniently a biodegradable material such as carbohydrate, high molecular weight vegetable oil, or gelatin with a suitable spectral window. This fluid is supplied adjacent the window at a pressure higher than the surrounding soil pressure, so it oozes into and fills the recess between window and soil at a flow rate sufficient to keep the window clear. Water alone may also be supplied periodically as a jet directed at the window, activated at or near the top of its arc of travel, to clean the window when soiled in a cleaning cycle.

Water may be also supplied by a jet from a water source to create a slurry by diffuse flow, which is then sucked by an aspirator into an internal flow cell with either a window or an ATR flow cell. Typically the flow is cyclically reversed to remove grit and soil from the aspirator holes, which may be the same size, preferred, or different.

Commercial flow cells are available which use ATR (attenuated total internal reflection) with MIR, although ATR is not essential it is very much preferred. ATR with NIR is somewhat problematic due to short path length, which is much shorter for NIR.

Diffuse reflectance gives signals affected by scattering, requiring mathematical transformation; direct absorbance gives a clear signal; and direct reflectance may have effects from the real part of refractive index. In general spectra are quantitatively comparable only when measured by the same method; it is possible to use different methods as input to a common data vector.

The flow cells may provide liquid samples on either side of the window. The soil samples are primarily suspended rather than dissolved as there is not time for complete solution to occur. It is possible to measure pesticides and other low level contaminants as well as constituents by providing an add-on molecular layer which preferentially adsorbs the target contaminant molecule(s). If repeat measurements are desired the adsorbed contaminant or pesticide must be flushed from the molecular layer by a suitable system such as those developed in high pressure liquid chromatography.

The emitter can be geared to Raman or absorbance spectroscopy. Raman spectroscopy can utilize a wide range of quasimonochromatic sources such as any laser line in the UV, visible and NIR range will do, with a narrow frequency range of about 0.1 nm or less, a favored gas laser wavelength is 515 (strictly 514.5) nm (Argon), gas lasers can be used for more precision, or an LED laser, which has a resonant cavity to reduce bandwidth from an LED source, in conjunction with at least one band pass filters, or an LED source with preferably two band pass filters. Thermal sources provide a continuous distribution of radiation from UV to MIR, limited only by choice of window material, if any. Semiconductor sources are available for wavelengths shorter than about 6 µm, each covering a limited wavelength range. In general semiconductor sources provide higher photon flux, but only over a limited wavelength range. Semiconductor sources are preferred for measurement of a single known analyte. Thermal sources are preferred for measurement of several analytes over a broad spectral range. As Raman response is proportional to the fourth power of frequency, the exciting frequency is preferred as high as possible as long as it does not generate fluorescence in material under investigation The detectors may be photoconductive, photoelectric, or bolometric, commercial off-the-shelf devices are readily available. A spectral differentiator is present typically a prism grating or spectrometer. Although in theory Raman and NIR have the same set up, Raman has much lower amplitude. The Raman detector includes a prism or a multiple grating to differentiate wavelengths coupled with a sensitive photon counter and an amplifier, such as a photomultiplier, an avalanche photodiode or equivalent. The NIR detector includes a movable grating or prism associated with a single detector, or a fixed grating or prism with a multi element detector. The MIR detectors could be similar in structure to the NIR detectors without a prism, but may also be a Fourier transform spectrometer; the wavelengths are distinct from the NIR ones.

The window, which rotates with the coulter, needs a reference target, such as standard black and white line pattern, to calibrate sensor response, and correct for sensor drift or muck on the window abrasion or other damage to the window. The target is mounted at or near the top of the coulter typically on the axle frame. If the target response measured by the sensor changes, then the window must be checked. This is expected to be rare, though this is currently unverified.

The coulter is typically between 12 and 15 millimeters (about ½ to ⅝ in) thick, but may be thinner, a wide range of coulters are available If the flow cell concept is utilized, a pH meter and an electroconductivity meter can be incorporated. Calibration is maintained by purging and a buffer solution. The coulter itself can incorporate a strain gauge to measure viscoelastic soil response. Raman and IR complement each other functionally as they measure spectral features some of which are distinct, and some of which are common, depending on sample molecular symmetry. Scattering can be used to measure soil condition (texture).

GPS would be mounted in the air on the tractor or seeder, plus an optical encoder measuring angular displacement of the window of coulter, enabling calculation of the precise position of the sensor, giving ground depth and surface position relative to the GPS position.

The depth of alternative systems such as a horizontal cultivator at fixed depth, typical 10 cm (4 in), the optimal working depth which varies with soil moisture, up to 30 cm (12 in), or less. The coulter of the invention typically operates from the surface 0 cm to depths of 20 to 30 cm, including all intermediate depths for agricultural application. Larger coulters and depths may be used for environmental applications.

Sampling density can be adjusted, practically to each millisecond, (tractor speed 3 meter/second or 11 km/hour, sampling every 3 cm, continuously with more than one sensor) controlled by sensor response time, which can be improved by using faster electronics and clock speed. Above ten gigahertz boundary problems can be expected as this frequency is technically infeasible (at a reasonable commercial price).

The structure mounting the coulter of the invention is quite different from a seeder and its seeding coulter which has a depth of typically 1 to 5 cm (½ to 2 in).

The signals from spectral measurements are transmitted to a data processing apparatus, which uses conventional statistical models to infer the presence or absence of a constituent or the like component. The supplied information includes the amplitude at specific wavelengths from the detector(s). The optical amplitudes, which are preferably mean centered and normalized, can be used as absolute values, when subjected to multivariate analysis. It is understood to those skilled in the art that multivariate analysis is a form of factorial analysis originally derived from analysis of covariance, such as Principal Component Analysis (PCA), Neural Networks (NN), Linear Discriminant Analysis (LDA), Partial Least Squares (PLS) and similar algorithms. In this particular application the absorption band curves for the constituent components tested are well known in the art and can be utilized as calibration references.

DESCRIPTION OF THE PREFERRED EMBODIMENTS

Figure 1:
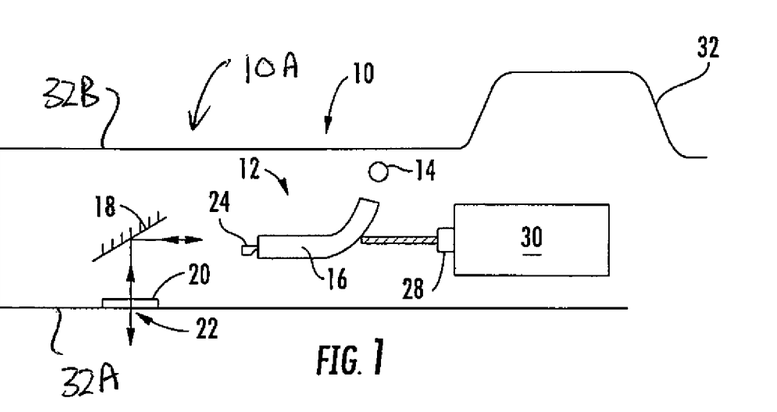
FIG. 1 shows a top sectional view of the coulter of the invention.
Figure 2:
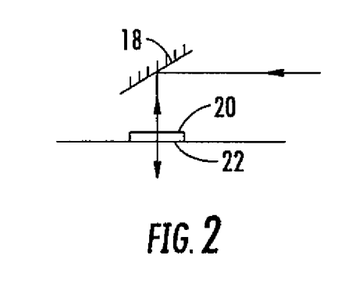
FIG. 2 shows a detail of the window of the invention.
Figure 3:
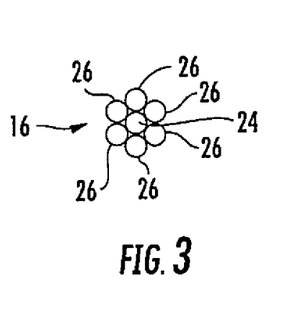
FIG. 3 shows an end elevational view of the detector of the invention.
Figure 4:
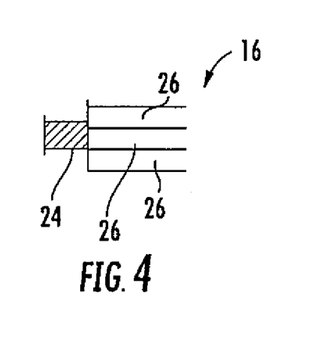
FIG. 4 shows a side elevational view of the detector of the invention.
Figure 5:
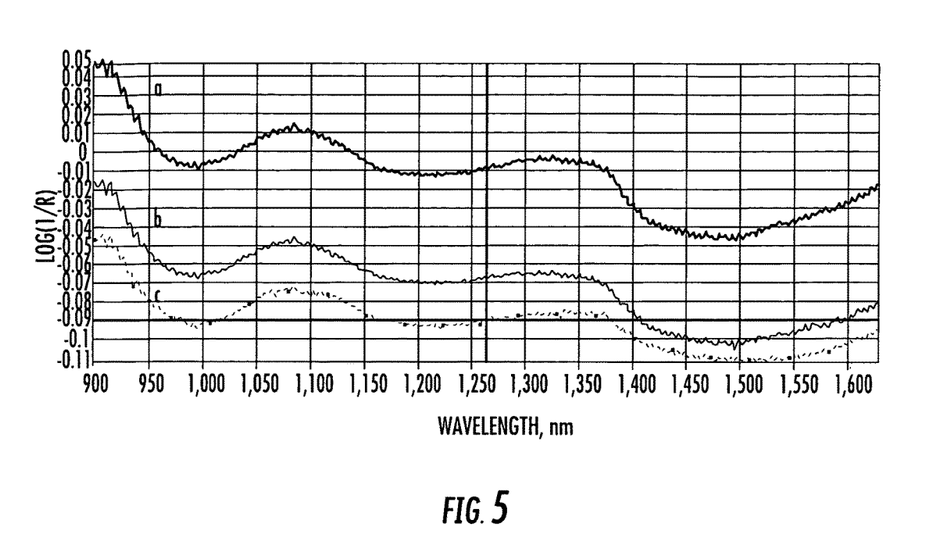
FIG. 5 shows three spectra measured by the device of FIG. 1 (Lab I) at different depths.
Figure 6:
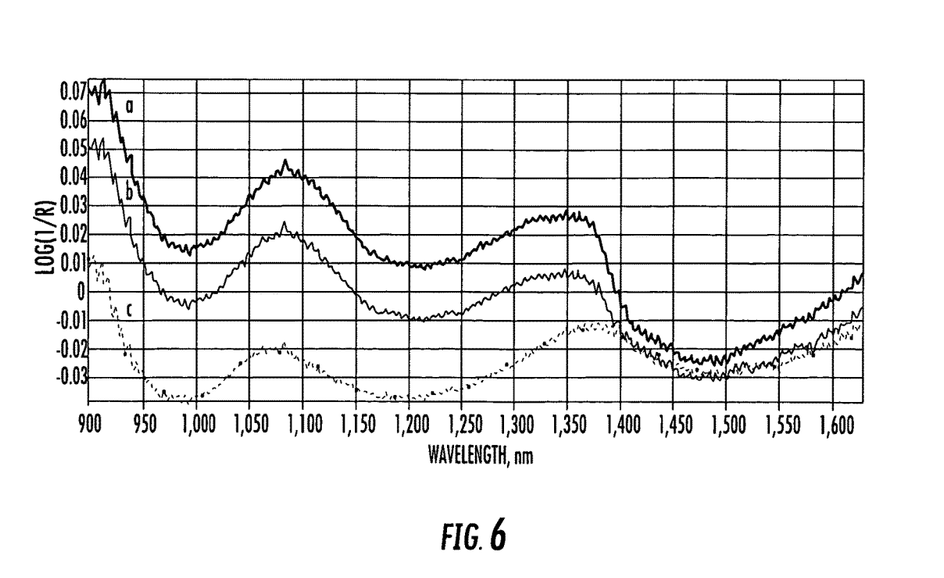
FIG. 6 shows another three spectra measured by the device of FIG. 1 (Lab II) at different depths.
Figure 7:
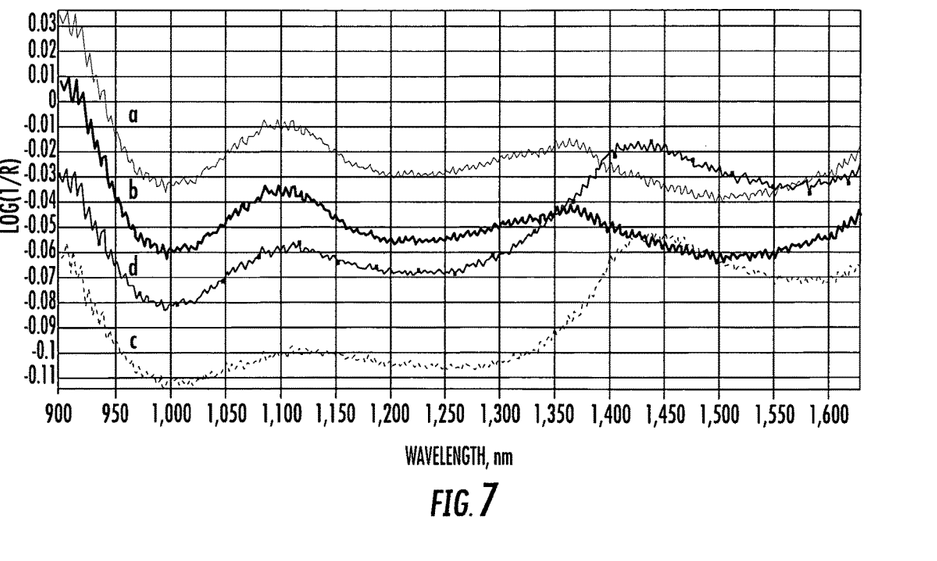
FIG. 7 shows four spectra measured by the device of FIG. 1 (Lab III) at different depths.

The invention is now further illustrated by reference to preferred embodiments thereof. In the first example illustrated in FIGS. 1 to 7, numeral 10 indicates a coulter of the invention. The coulter 10 comprises a coulter disk 10A with an axle 32 and two side surfaces 32A and 32B. In a first embodiment a detector system 12 extends radially within the coulter disk 10A, output light is generated by quartz-halogen bulb 14, and is propagated through fiber optic bundle 16 to a mirror 18 and through an aperture 22 and a glass window 20 provided in the surface 32A as shown in FIG. 1. Aperture 22 and window 20 are ½ inch (12.5 mm) diameter. Fiber optic bundle 16 has six illuminating fiber optics 26 each 1000 mu m (1 mm) in diameter, with numerical aperture of about 0.5, transmitting light from a quartz halogen source, which emits over the indicated range 900 to 1800 nm). The Martech detector fiber 24 has a diameter of 1000 mu m (1 mm) and a numerical aperture of 0.5 and projects beyond the illuminating fibers, its detector face is 1 mm diameter. Optical detector fiber 24 is connected through input port 28 to spectrometer 30. A typical photodiode array detector is a chip, off-the-shelf, and typically about 20 mm long, up to 14 mm wide, and 2 to 5 mm thick, the chip's photosensitive pixel array, which is typically a single line of 256 to 2048 pixels, is about 50 microns across. The resolution of the spectrometer 30 is thought to be about 5 nm over the nominal range of 900 to 1800 nm, in practice as seen in the spectra the actual range is from 900 to about 1625 nm. Although a dedicated chip can be designed for the coulter it is convenient to use off-the shelf components. Output light passes through optical fiber bundle 16 and is reflected by Au front surface mirror 18 into aperture 22, returning input light is reflected by mirror 18 onto detector fiber 24. The spectra shown in FIGS. 5 to 7 were measured using the device of FIG. 1 in situ. The spectra of FIG. 5, lab I, site 1, were measured at different depths a at 19 cm, b at 27 cm and c at 38 cm. The spectra of FIG. 6, lab II, site 2, were measured at different depths a at 12 cm, b at 22 cm and c at 30 cm. The spectra of FIG. 7, lab III, site 3, were measured at different depths a at 12 cm, b at 31 cm, c at 34 cm and d at 36 cm. These results show scientifically reproducible quality spectra. This quality is sufficient for analytical purposes; the geological structure varies with depth as there are two, three or four different strata involved in each location. The convergence of spectra above 1400 nm in FIG. 6 is due to the presence of water in the soil. Basically the analysis compares the obtained spectra with known spectra of soil constituents, using the statistical methods outlined, which is sufficient to identify the presence and concentration of soil constituents.

Figure 8:
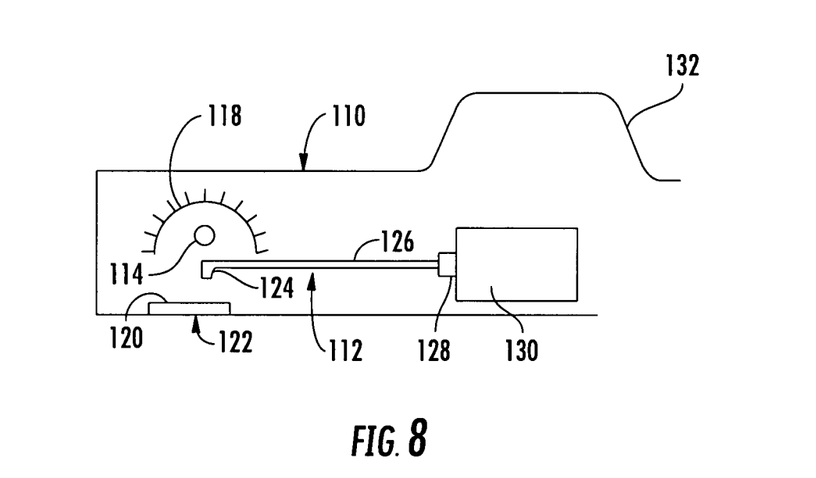
FIG. 8 shows an top sectional view of another coulter of the invention.
Figure 9:
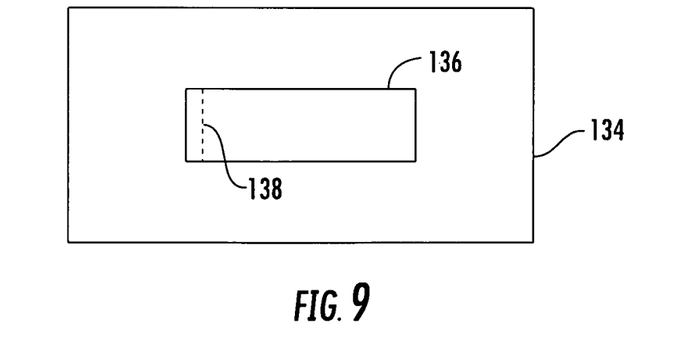
FIG. 9 shows a detail of the detector of the coulter of FIG. 8.
Figure 10:
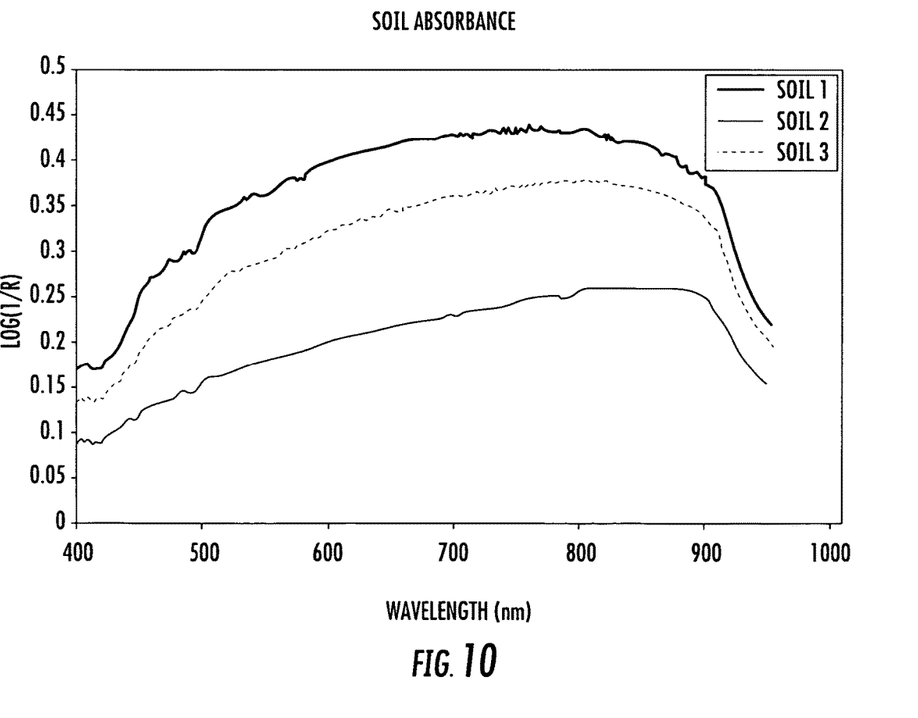
FIG. 10 shows three spectra of different soils measured by the device of FIG. 8.

In the second example illustrated in FIGS. 8 to 10 numeral 110 indicates another coulter of the invention. In a second embodiment detector system 112 extends radially of coulter 110, output light is emitted by halogen bulb 114, focussed by concave mirror 118 onto aperture 122 and sapphire window 120. Aperture 122 and window 120 are ½ inch (12.5 mm)

diameter. One end 124 of optical fiber cable 126 acts as light detector. Optical detector fiber 124 is connected through input port 128 to spectrometer 130. Spectrometer 130 was improvised having a diffraction grating and pixel array 134, of which all but portion 136 is masked. Portion 136 is divided into about 370 transverse trips 138, each strip is 1 pixel wide and about 80 to 100 pixels high or tall. Each strip corresponds to about 2 nm resolution. The individual pixel responses are measured and standardized. Two responses were registered for each strip, one that of a white plate or plaque (white response) the second with nothing (dark response) that is no or minimal light was reflected back. The reflectance was calculated from (reflected sample minus dark response) divided by (white response minus dark response) to give R reflectance. The reflectance at each wavelength is then transformed into log (1/R). It was found that the light from optical fiber cable 124 was sufficient and amplification was unnecessary. FIG. 10 shows three spectra from different soils. These results show scientifically reproducible quality spectra. Basically the analysis compares the obtained spectra with known spectra of soil constituents, using the statistical methods outlined, which is sufficient to identify the presence and concentration of soil constituents.

As those skilled in the art realize these preferred, disclosed and described details and materials and components can be subjected to substantial variation, modification, change, alteration and substitution without affecting or modifying the function of the described embodiments. Although specific embodiments of the invention are described above, it is not limited thereto. Numerous modifications and variations fall within the scope of the claimed, disclosed and described invention, as interpreted in the light of natural laws of science and engineering as understood by persons skilled in the art.

The invention claimed is:

1. Apparatus for measuring constituents in soil comprising:
   a coulter disk having two side surfaces and an axle frame mounting the coulter disk for rotation such that the coulter disk rotates as it passes along the soil and cuts into the soil;
   and at least one detector system comprising an electromagnetic radiation detector, a source of electromagnetic radiation, and a window transparent to electromagnetic radiation, wherein said source emits radiation through said window to said soil, and said detector receives radiation through said window reflected from said soil;
   wherein the detector system is mounted in an interior of the coulter disk;
   and wherein the window is mounted in one side surface of the coulter disk and rotates with the coulter disk.

2. The apparatus according to claim 1 wherein said at least one detector system comprises a plurality of detector systems at angularly spaced positions around the disk.

3. The apparatus according to claim 1 wherein said electromagnetic radiation is selected from the group consisting of UV radiation, visible radiation, near infrared radiation, mid infrared radiation, and Raman scattered radiation.

4. The apparatus according to claim 1 wherein said electromagnetic radiation detector comprises a spectrometer.

5. The apparatus according to claim 1 wherein there is a recess in said side surface of said coulter disk at said window and a nozzle for water to provide a jet of water to induce a slurry to form in said recess and an aspirator in said recess to suck said slurry through a flow cell in said coulter disk, said window forming a wall of said flow cell, and a channel from said flow cell to an external orifice in said coulter disk.

6. A method for measuring constituents in soil comprising:
   mounting a coulter disk having two side surfaces for rotation on an axle frame;
   operating the coulter disk such that the coulter disk rotates as it passes along the soil and cuts into the soil;
   providing at least one detector system comprising an electromagnetic radiation detector, a source of electromagnetic radiation, and a window transparent to electromagnetic radiation, wherein said source emits radiation through said window to said soil, and said detector receives radiation through said window reflected from said soil;
   wherein the detector system is mounted in an interior of the coulter disk;
   and wherein the window is mounted in one side surface of the coulter disk and rotates with the coulter disk to positions above and below a surface of the soil.

7. The method according to claim 6 wherein said at least one detector system comprises a plurality of detector systems at angularly spaced positions around the disk.

8. The method according to claim 6 wherein said electromagnetic radiation is selected from the group consisting of UV radiation, visible radiation, near infrared radiation, mid infrared radiation, and Raman scattered radiation.

9. The method according to claim 6 wherein said electromagnetic radiation detector comprises a spectrometer.

10. The method according to claim 6 wherein there is a recess in said side surface of said coulter disk at said window and a nozzle for water to provide a jet of water to induce a slurry to form in said recess and an aspirator in said recess to suck said slurry through a flow cell in said coulter disk, said window forming a wall of said flow cell, and a channel from said flow cell to an external orifice in said coulter disk.

11. The method according to claim 6 including the step of determining the concentration of constituents in soil the as a function of depth.

12. The method according to claim 6 wherein the coulter cuts smoothly into the soil with minimal disturbance.

13. The method according to claim 6 including measuring angular displacement of the window of coulter disk thus enabling calculation of the position of the sensor to provide an indication of ground depth and surface position relative to the GPS position.

14. The method according to claim 6 including the step of measuring output amplitudes of the radiation as a function of wavelength and the step of comparing the output amplitudes to input amplitudes as a function of wavelength as ratios to generate a characteristic spectrum the step of comparing said output spectrum to known output spectra generated by standard samples of known constituents by multivariate analysis thereby identifying the presence and concentration of said constituents.

15. The method according to claim 6 wherein resultant output electromagnetic radiation is generated by a step selected from group consisting of diffuse reflectance from soil, transmission through a soil slurry in a flow cell, and attenuated total internal reflection at a window soil slurry interface of a flow cell and Raman scattering.

16. The method according to claim 6 including the step of separately calculating an output amplitude for a narrow interval of wavelength to give an absorbance value for each said wavelength interval.

17. The method according to claim 6 wherein including the step of dispersing said output electromagnetic radiation through a wavelength selector to separate it into distinct wavelength intervals and the further step of measuring the amplitudes of the distinct wavelength intervals.

18. The method according to claim 6 comprising the step of collimating the input electromagnetic radiation.

19. The method according to claim 6 comprising the step of collimating the output electromagnetic radiation.

* * * * *